(12) United States Patent
Maeda

(10) Patent No.: US 6,507,752 B1
(45) Date of Patent: Jan. 14, 2003

(54) METHOD OF QUANTITATIVE DETERMINATION OF CARDIAC MUSCLE CONTRACTION BY ELECTROCARDIOGRAM-SYNCHRONIZED TRANSVERSE TOMOGRAM

(76) Inventor: Hisatoshi Maeda, 5-7, Kibougaoka 4-chome, Chikusa-ku, Nagoya-shi, Aichi, 464-0016 (JP)

( * ) Notice: Subject to any disclaimer, the term of this patent is extended or adjusted under 35 U.S.C. 154(b) by 0 days.

(21) Appl. No.: 09/646,903
(22) PCT Filed: Aug. 17, 1998
(86) PCT No.: PCT/JP98/03653
   § 371 (c)(1),
   (2), (4) Date: Oct. 10, 2000
(87) PCT Pub. No.: WO99/64890
   PCT Pub. Date: Dec. 16, 1999

(30) Foreign Application Priority Data
Jun. 9, 1998 (JP) .......................................... 10-197945

(51) Int. Cl.[7] .................................................. A61B 5/05
(52) U.S. Cl. ...................................... 600/436; 600/428
(58) Field of Search ................................ 600/428, 407, 600/408, 436, 431; 345/419, 418; 250/362, 363.01, 363.02, 363.03, 363.04, 363.07, 370.08; 378/41; 128/922

(56) References Cited

U.S. PATENT DOCUMENTS 5,803,914 A * 9/1998 Ryals et al. ................. 600/407

FOREIGN PATENT DOCUMENTS

| JP | 4-270983 | 9/1992 |
| JP | 5-120428 | 5/1993 |
| JP | 8-146139 | 6/1996 |
| JP | 9-43354 | 2/1997 |

\* cited by examiner

Primary Examiner—Marvin M. Lateef
Assistant Examiner—Eleni Mantis Mercader
(74) Attorney, Agent, or Firm—Oblon, Spivak, McClelland, Maier & Neustadt, P.C.

(57) ABSTRACT

From ECG-gated SPECT or PET images of radioactive myocardial perfusion imaging agents, contraction of the myocardium along the tangential direction, i.e., in the direction parallel to the myocardium, can be evaluated. The amount of the agents which accumulate in the heart muscle is calculated from reconstructed short-axis ECG-gated images and is projected on a virtual cylindrical screen whose axis is the same as the long axis of the heart. Spatial and temporal changes in time and space in the projected count distribution on the screen are described by a two-dimensional second order differential equation, which is called an equation of continuity for the fluid. This equation can be solved numerically with a computer. The displacements of points on the myocardium in the tangential direction are calculated by projecting the displacement of each point back onto the cardiac wall. From these displacements, contraction and expansion of the heart muscle can be quantified.

2 Claims, 2 Drawing Sheets

METHOD OF QUANTITATIVE DETERMINATION OF CARDIAC MUSCLE CONTRACTION BY ELECTROCARDIOGRAM-SYNCHRONIZED TRANSVERSE TOMOGRAM

BACKGROUND OF THE INVENTION

1. Filed of Invention

This invention relates to a method of evaluating segmental myocardial function from a value of contraction which is calculated from short-axis images of count distribution using radioactive myocardial perfusion imaging agents which accumulate in human heart after intravenous injection, and by using a rotating gamma camera under, electrocardiographic (ECG) gating.

2. Related Art

Assessment of myocardial function by using radioactive myocardial perfusion imaging agents has been frequently employed. This method includes estimation of myocardial wholesomeness by measuring myocardial blood perfusion and metabolism from the extent of accumulation of these agents. There are two widely employed techniques to evaluate the amount of accumulations: single photon emission computed tomography (SPECT) and positron emission computed tomography (PET). In both techniques, data are acquired from multiple angles around the object and transverse images are obtained. These techniques have advantages of acquiring more information than conventional planar images.

Another technique to assess the segmental cardiac function is to analyze ECG-gated images which are obtained by dividing one cardiac cycle into equally divided multiple time intervals. This ECG-gated technique enables us to obtain sequential SPECT or PET images from end-diastolic to end-systolic phases.

Changes in the wall thickness from diastole to systole are often employed to assess the myocardial function (maximum count method, K Narita, Kakulgaku 33 617–28, 1996, K Fukuchi, J Nuclear Medicine, 38 1067–73, 1997). Other methods to assess the cardiac function include: volume changes calculated using the edge-detection technique by thresholding, or by Gaussian approximation of the count distribution, or by approximating the contour of the inner surface of the chamber by a curve fitting (K Narita, Kakulgaku, 32, 1227–39, 1995, S Kumita, Kakulgaku, 33 1189–96, 1996, EG Depuey, J Nuclear Medicine 36, 952–5, 1995, Porenta, J Nuclear Medicine 36 1123–9, 1995), or by inspection of the epicardium by using three-dimensional animation of the wall motions.

In the maximum count method, the maximum count is determined by manually setting a region of interest (ROI), or by automatically picking up the maximum count along a line radiating radially from the center. However, there is debate that the point where the maximum count is measured at the systolic phase does not locate at the same position on the myocardium at the diastolic phase; also, the maximum count does not always indicate the thickness of the wall. The volumetric method has disadvantages of vagueness in determining the inner and the outer borders of the wall (I Buvat J Nuclear Medicine, 38 324–9 1997), and obtaining knowledge of the segmental wall function is therefore difficult.

The main purpose of the three-dimensional animation analysis is to study visually the wall motion which is centripetal, i.e., displacement of wall perpendicular to the wall. Poor wall motion which is observed by this method is not parallel to the wall, and therefore does not always indicate reduction of cardiac function at the point.

It is necessary to analyze the contraction parallel to the cardiac wall, because the muscle fibers are running nearly parallel to the cardiac wall. In this invention, muscle contractions parallel to the cardiac wall are evaluated from the displacement of each point on the wall by using images obtain by SPECT and PET.

SUMMARY OF THE INVENTION

From ECG-gated SPECT or PET images of radioactive myocardial perfusion imaging agents, contraction of the myocardium along the tangential direction, i.e., in the direction parallel to the myocardium, can be evaluated. The amount of the agents which accumulate in the heart muscle is calculated from reconstructed short-axis ECG-gated images and is projected on a virtual cylindrical screen whose axis is the same as the long axis of the heart. Spatial and temporal changes in time and space in the projected count distribution on the screen are described by a two-dimensional second order differential equation, which is called an equation of continuity for the fluid. This equation can be solved numerically with a computer. The displacements of points on the myocardium in the tangential direction are calculated by projecting the displacement of each point back onto the cardiac wall. From these displacements, contraction and expansion of the heart muscle can be quantified.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3A shows the count distribution of the second phase on the unfolded cylindrical screen and FIG. 3B shows the differences of the count distribution between the third- and the second-phase images, multiplied by 5 to emphasize the contrasts, and where ba indicates the apex, p the posterior wall, s the septum, an the anterior wall and 1 the lateral wall.

DETAILED DESCRIPTION OF THE INVENTION

Image data are obtained from 360 degrees around a subject with the R-wave trigger of ECG. From the data, the transverse images are constructed, and the short- and long-axis images are reconstructed after manual or automatic determination of the long axis. These processes are usually performed by a dedicated computer and software bundled with commercially available gamma-camera systems.

Equations for the long axis are calculated for each phase from the positions of the centers of these short-axis images using the least square fit. The center of each image is determined using the method of center of gravity, or approximation of a circle or an ellipse.

Figure 1:
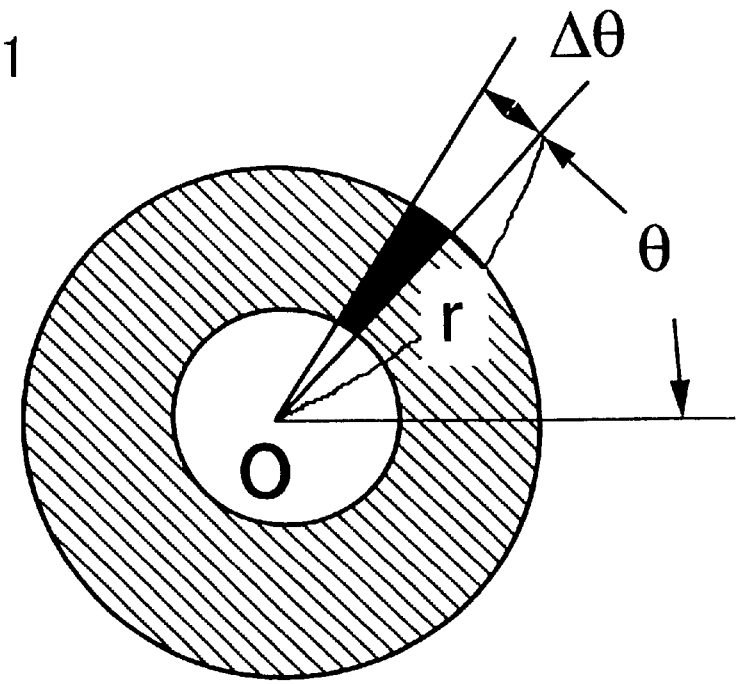
FIG. 1 is a schema of integration to project a count distribution of a short-axis image on a cylindrical screen using a cylindrical coordinate system.

The short-axis images are equally divided into multiple fan-shaped regions with an apical angle ($\Delta\theta$) around the origin (O, FIG. 1), which is defined as the intersection of the long axis and the image plane. Let the count distribution on the short-axis image be denoted as $P(r,\theta,z,t)$, in which $\theta$=angle around the origin, r=distance from the center, z=distance along the z direction parallel to the direction from apex to base, and t=time. Count distribution per unit angle is given by equation (1) using the cylindrical coordinate system as, $$\rho(\theta, z, t) = \frac{1}{\Delta\theta} \int_0^{r_{max}} d\xi \int_\theta^{\theta+\Delta\theta} \xi P(\xi, \varsigma, z, t) d\varsigma. \tag{1}$$

The integration in r goes from O to $r_{max}$, which is large enough to cover the image.

Figure 2:
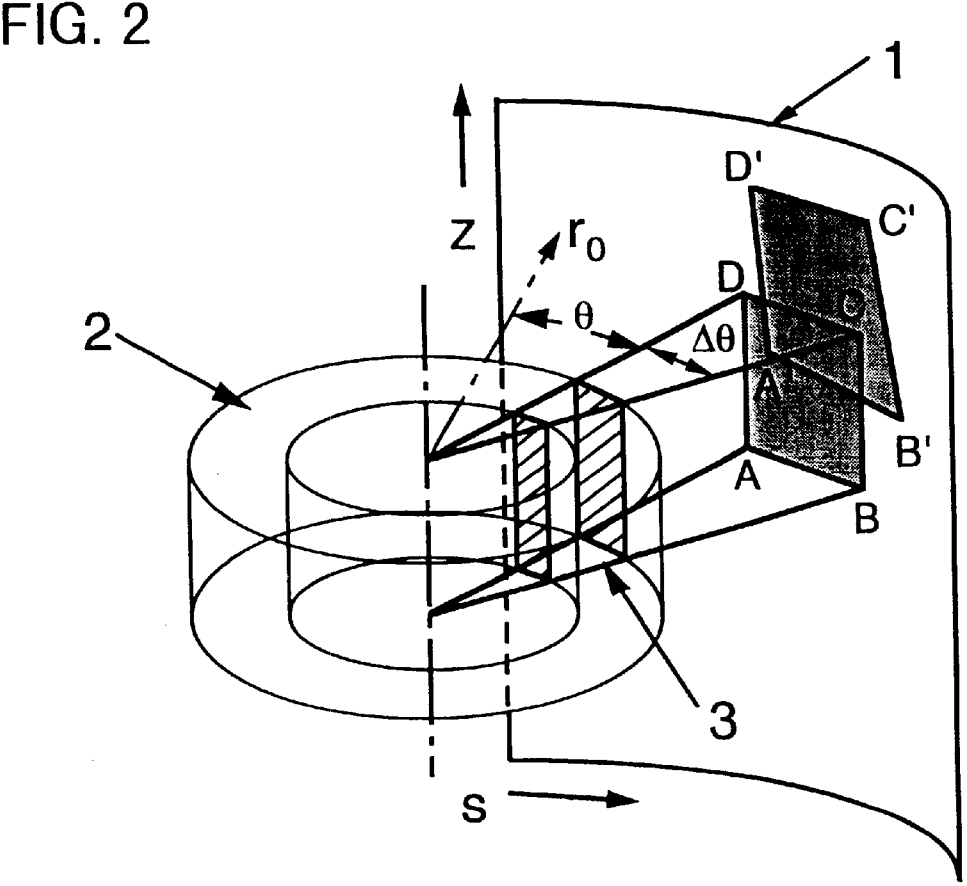
FIG. 2 is a drawing of projection of a count distribution on a cylindrical screen whose long axis is the same as the long axis of the heart, and a projected rectangle ABCD changes its shape to A'B'C'D' after translation and rotation of the heart where 2 is a cardiac muscle on a short-axis image, and 3 is a region to be integrated on a slice.
Figure 3A:
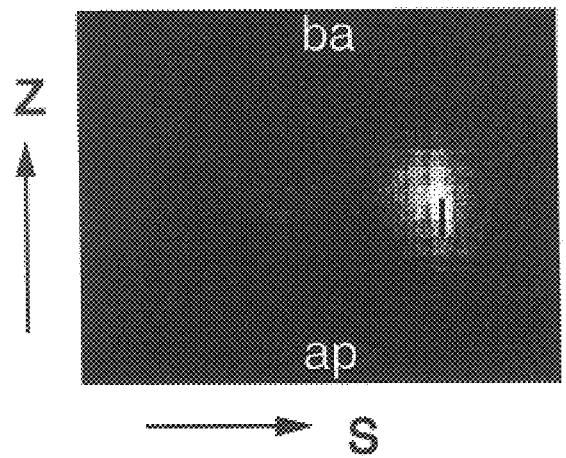
FIGS. 3A and 3B are intermediate images during computation: ECG-gated SPECT images from a patient with 50% to 90% stenoses of right coronary artery, left anterior descending artery and left circumflex artery, where

The values obtained from the foregoing integration are projected on a virtual cylindrical screen (FIG. 2), whose axis is the same as the long axis of the heart, and whose diameter is equal to $r_o$. Let the distance along the circumferential direction (along the tangential direction on the cylindrical screen) be s ($s=r_0\theta$), and let the count distribution on the screen be $\sigma(s,z,t)$. FIG. 3A depicts a projected count distribution on the unfolded cylindrical screen, $\sigma(s,z,t)$, calculated using data from a patient.

Figure 3B:
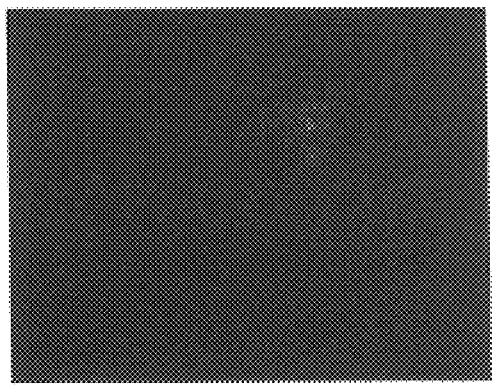

Let the side lengths of a small rectangle ABCD on the screen (FIG. 2) AB and AD be equal to $\Delta s$ and $\Delta z$. When this rectangle changes its shape to A'B'C'D' as the heart contracts, the area of the rectangle ABCD changes from $\Delta s \Delta z$ to $(1+v_{s,s}\Delta t +v_{z,z}\Delta t) \Delta s \Delta z$ from time t to $t+\Delta t$, in which $v_s$, $v_z$, $v_{s,s}$ and $v_{z,z}$ denote the speed of displacement and their partial derivatives with respect to s and z. The terms higher than the third orders in $\Delta$ are ignored. The total counts in the rectangle ABCD at time t are given as $\sigma(s,z,t) \Delta s \Delta z$, which becomes $\sigma(s+v_s\Delta t, z+v_z\Delta t, t+\Delta t)\times(1+v_{s,s}\Delta t+v_{z,z}\Delta t) \Delta s \Delta z$ at time $t+\Delta t$ in the rectangle A'B'C'D'. The total counts in ABCD and A'B'C'D' should be the same because the rectangles ABCD and A'B'C'D' reside on the same area on the cardiac wall, and because in the myocardium no perfusion imaging agent dislocates, is produced, or is removed due to cardiac contraction during the study. Thus we can set $\sigma(s+v_s\Delta t, z+v_z\Delta t, t+\Delta t)\times(1+v_{s,s}\Delta t+v_{z,z}\Delta t)=\sigma(s, z, t)$, which becomes $\sigma_s v_s + \sigma v_{s,s} + \sigma_z v_z + \sigma v_{z,z} = -\sigma_{,t}$ after ignoring the terms higher than the third orders in $\Delta$. This equation is called an equation of continuity for the fluid. $\sigma_{,s}$ and $\sigma_{,z}$ are the partial derivatives of $\sigma$ in s and z in $\sigma$ and z. FIG. 3B shows $\sigma_{,t}\Delta t$, the difference of the count distribution between the two successive phases shown in FIG. 3A.

Define a flow potential given as, $$\frac{\partial \psi}{\partial s} = \sigma v_s, \text{ and } \frac{\partial \psi}{\partial z} = \sigma v_z \tag{2}$$

and the following equation is derived, $$\frac{\partial^2 \psi}{\partial s^2} + \frac{\partial^2 \psi}{\partial z^2} = -\frac{\partial \sigma}{\partial t} \tag{3}$$

This second order differential equation describing the liquid flow can be solved numerically with a computer using a finite-element method, or Fourier analysis, or a difference equation (Morse and Feshbach, Method of Theoretical Physics, McGraw-Hill; New York, pp692–710, 1953).

Since the changes in the distribution of radioactive myocardial perfusion agents in the myocardium can be mathematically described as a two-dimensional fluid on the cylindrical screen, we can calculate the displacement of each point on the screen as a particle of the fluid, and the displacement of a point on the screen can be back-projected onto the myocardium. The contraction of the heart muscle is calculated as the changes in the distances between the two arbitrary points.

By solving the equation of two-dimensional flow (3) numerically with a computer, $v_s$ and $v_z$ can be evaluated as $$V_S = \frac{1}{\sigma} \frac{\partial \psi}{\partial S}, \text{ and } V_Z = \frac{1}{\sigma} \frac{\partial \psi}{\partial Z} \tag{4}$$

Denoting the end diastolic phase by the subscript 1, the displacements in the s and z directions in the nth phase are, $$s_n = s_1 + \sum_{k=1}^{n-1} s_z(s_k, z_k)\Delta\tau \tag{5}$$

$$z_n = z_1 + \sum_{k=1}^{n-1} v_z(s_k, z_k)\Delta\tau,$$

where $\Delta\tau$ is the time interval between the two phases.

It is necessary to project the on-screen displacement back onto the cardiac wall. We choose the average distance of the count distribution $\bar{r}$ defined by the following expression:

$$\bar{r} = \frac{\int_0^{r_{max}} \int_\theta^{\theta+\Delta\theta} d\varsigma \xi^2 P(\xi, \varsigma, z, t) d\xi}{\int_0^{r_{max}} \int_\theta^{\theta+\Delta\theta} d\varsigma \xi P(\xi, \varsigma, z, t) d\xi} \tag{6}$$

as the distance from the origin (O) to the muscle. The on-screen point ($s^n$, $z_n$) corresponding to a point on the cardiac wall is calculated using equation (6) as ($\bar{r}_n$, $\theta_n$, $z_n$) on the cylindrical coordinate system, in which $\theta_n=s_n/r_0$, and $\bar{r}_n$ is the value obtained by computing equation (6) in the direction $\theta=\theta_n$. Displacement of a point from ($\bar{r}_1$, $\theta_1$, $z_1$) in the diastolic phase to ($\bar{r}n$, $\theta_{n,\ zn}$) in the nth phase is calculated by using equations (5) and (6).

In equations (1) through (6), s and z are treated as continuous variables. However, in the actual images used in nuclear medicine, these images consist of a finite number of pixels, and therefore the parameters (s, z) must be substituted with the discrete integers (i, j), where i=1, 2, . . . , m, and j =1, 2, . . . , 1, with m and 1 are the matrix size on the virtual screen. The value of $\psi(i, j)$s are computed by replacing the right hand side of equation (3) with the difference between two images with successive phases. The speeds of displacement $v_s(i, j)$ and $v_z(i, j)$ are calculated from the difference of $\psi(i, j)$ by using equation (4), but when $\sigma(i, j)$ is zero or close to zero, $v_s(i, j)$ and $v_z(i, j)$ cannot be calculated. Thus we set $\sigma=0.1\ \sigma_{max}$ when $\sigma<0.1\sigma_{max}$, in which $\sigma_{max}$=maximum value of $\sigma$. Setting the position of a pixel (i, j) at the end diastole as $(s_1(i, j), z_1(i, j))=(i, j)$, the position on the nth phase $(s_n(i, j), z_n(i, j))$ is given by the following equation as:

$$s_n(i, j) = i + \sum_{k=1}^{n-1} v_s(s_k(i, j), z_k(i, j))\Delta\tau$$

$$z_n(i, j) = j + \sum_{k=1}^{n-1} v_z(s_k(i, j), z_k(i, j))\Delta\tau$$

(7)

Because $s_n(i, j)$ and $z_n(i, j)$ are not always an integer, $v_s$ and $v_z$ at the point $(s_n(i, j), z_n(i, j))$ are interpolated from four adjacent pixels.

Letting the area of a rectangle defined by four points (i, j), (i+1, j), (i, j+1) and (i+1, j+1) at the end diastole be unitary, at the nth phase the area becomes approximated by $$\bar{r}_n(i, j)/\bar{r}_1(i, j)(s_n(i+1, j)-s_n(i, j))(z_n(i, j+1)-z_n(i, j))$$

Figure 4:
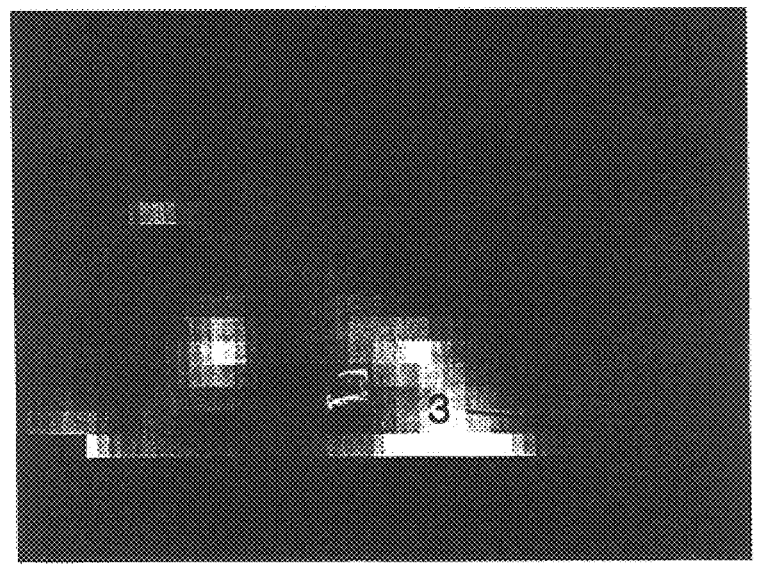
FIG. 4 is a drawing showing the distribution of contraction and expansion on the third phase calculated by setting the pixel size of the first phase as unitary, where 1 indicates decreased contraction on the basal to lateral wall, 2 on the posterior wall, and 3 on the apical to the posterolateral wall; the contractions of the muscle are spread to all over the heart at the end systolic phase and these abnormal regions are thought to be due to conduction delays.

(8)

where $\bar{r}_n(i+1, j) \equiv \bar{r}_n(i, j), (\bar{r}_n(i, j+1)-\bar{r}_n(i, j))$ and $(s_n(i, j+1)-s_n(i, j))$ are ignored. FIG. 4 shows the segmental contraction and expansion computed from equation (8). By setting an ROI on this image, segmental contraction can be measured.

Advantages and Effects of the Invention Compared with Related Art

In the maximum count method, contraction of the muscles is calculated from the change in the thickness perpendicular to the wall surface. Because the heart translates and rotates as it beats, and because measurements are performed on external coordinate systems, the point measured in the diastolic phase does not necessary locate at the same point in the systolic phase. In the three-dimensional animation technique, only the motion perpendicular to the wall can be analyzed. In the present invention, uncertainty regarding the location of measurements due to translational or rotational motions of the heart can be eliminated. Displacement of each point is calculated successively for each phase, and the contraction is evaluated from these displacements, which means the contraction is evaluated on a coordinate system fixed on the cardiac wall.

By using this invention, contraction can be evaluated in the tangential direction along the cardiac wall, which has not been possible with the conventional techniques using radionuclide perfusion agents. Because the data on the whole images are used, this method can be applied to noisy images with a low signal-to-noise ratio.

Effects on the Clinical Uses of the Invention

The contraction and expansion can be calculated numerically along the tangential direction at an arbitrary point and in an arbitrary area on the cardiac wall. We can apply this method not only to evaluate changes in the rate of contraction, but also to quantify how contraction spreads along the cardiac wall, including contraction abnormalities and contraction delays, and can apply it in clinical uses as a new method.

I claim:

1. A method for calculating an amount of dislocation of a plurality of points on a myocardium in a tangential direction along a cardiac wall in a human subject, by numerical calculations, comprising the steps of:

projecting a count distribution on a short-axis ECG-gated SPECT or PET image using a myocardial perfusion imaging agent onto a virtual cylindrical screen having a same axis as the heart;

unfolding said cylindrical screen into a plane;

expressing spatial and temporal changes of said count distribution on said cylindrical screen using a two-dimensional second-order differential equation by treating said changes as a two-dimensional liquid flow; and evaluating said projection of displacement of each of said plurality of points by solving said differential equation numerically.

2. The method as recited in claim 1, further comprising the step of:

quantifying contraction of the cardiac wall in the tangential direction from a difference in an amount of contraction from displacement on the cylindrical screen of the cardiac wall.

* * * * *